United States Patent [19]

Rosenshein et al.

[11] Patent Number: 5,412,561
[45] Date of Patent: May 2, 1995

[54] METHOD OF ANALYSIS OF SERIAL VISUAL FIELDS

[76] Inventors: Joseph S. Rosenshein, 1027 Barton Dr., #101, Ann Arbor, Mich. 48105; Marshall N. Cyrlin, 6200 Northfield Rd., West Bloomfield, Mich. 48322

[21] Appl. No.: 826,629

[22] Filed: Jan. 28, 1992

[51] Int. Cl.[6] .............................................. G06F 15/42
[52] U.S. Cl. .......................... 364/413.02; 364/413.01; 128/745; 606/4; 607/91; 607/93; 382/128; 351/226; 351/246
[58] Field of Search ...................... 364/413.02, 413.01; 128/745; 606/2, 4; 607/88, 91, 93; 382/2, 6; 351/222, 224, 226, 246

[56] References Cited

PUBLICATIONS

*Perimeter Digest*, H. Bebie et. al., Interzeag AG, 8952 Schlieren, Switzerland, 1983, pp. 1–50.
*The Field Analyzer Primer*, Second Edition, Allergan Humphrey, 1987, pp. 1–37.
*New Software Releases for the Humphrey Field Analyzer and STATPAC +PLUS TM*, Allergan Humphrey, San Leandro, Calif., Oct., 1988 pp. 1–18.
*New Releases for the Humphrey Field Analyzer, Introducing STATPAC 2* Allergan Humphrey, San Leandro, Calif., 1989, pp. 1–25.

ARVO Annual Meeting Abstract Issue, Mar. 15, 1990, vol. 31, No. 4, p. 15, No. 68–40.
"New Methods of Analysis of Serial Visual Fields", Marshall Curlin et al., May 3, 1991.
International Perimetric Society Meeting Display, Malmo, Sweden, Jun., 1990. (Photograph & copies of display).

*Primary Examiner*—Gail O. Hayes
*Assistant Examiner*—Gita Shingala
*Attorney, Agent, or Firm*—Basile and Hanlon

[57] ABSTRACT

A method of analyzing serial automated visual field data calculates a total field vector of the threshold sensitivity of points in a visual field and compares the total field vector with a calculated normal field vector for a given patient. The vector angle between the total field vector and the normal field vector is calculated to determine the distribution of threshold sensitivities to characterize the localization and the magnitude of field changes. In one embodiment, the sensitivities of each point in the visual field with respect to normal sensitivities for each point is plotted for each of a series of time spaced visual field tests. The single plot uses a line symmetrical about a zero axis whose magnitude reflects the difference from the norm for each point in each exam and forms a graphic depiction of changes in the visual field at each point over a series of visual field tests. Linear regression analysis is performed on the visual field data and provides an indication of trends of visual field changes.

8 Claims, 12 Drawing Sheets

EYE:OD
SGD W/LINEAR REG. CHI SQ. TEST
COPYRIGHT 1990. CORD. SINAI HOSP.,DET.
LOSS/IMPROVE. LIMITS (dB/YR.):0.2/0.2
CHANGE BASIS:AGE ADJUSTED NORMS
Y-SCALE: 4dB/SYMMETRIC PIXEL DISPLACEMENT

EXAM: 072286a 090487c 042588e 022789g 112789i 040290k
      040887b  091007d  090908f  030189h 012590j 052490l
RMS:  0.9 1.3  1.6 3.4  1.9 3.3  3.1 1.1  3.9 1.7  3.1 3.5
PUPIL: 1.0 2.0  1.5 2.5  3.0 2.0  1.0 1.0  1.0 3.8  1.0 1.0

FIG·10

METHOD OF ANALYSIS OF SERIAL VISUAL FIELDS

BACKGROUND OF THE INVENTION

1. Field of the Invention

The present invention relates, in general, to methods of diagnosing eye disorders and, more specifically, to methods of diagnosing eye disorders using visual field analysis derived from perimeter field testing.

2. Description of the Art

Visual field testing is used by eye care practitioners to obtain information about the diagnosis and progress of major blindness-causing diseases. For example, field testing is used as a primary tool in diagnosing and monitoring glaucoma.

The normal visual field in an eye extends in varying angular degrees over the eye. Visual sensitivity is greatest in the center of the eye, or at the fovea, and decreases toward the periphery. The field of vision can be represented as a hill or island which, in a normal state, has a generally smooth shape. Field defects characteristic of certain diseases are easily seen as any statistically significant departure from the smooth shape of the normal hill or island of vision. Field defects can be localized, or there may be a general depression of the whole field.

Static or kinetic perimetry testing derived from or based on the well-known Goldmann perimeter is used to determine the variations from normalcy from any individual visual field. In static perimetry testing, the differential light sensitivity at a series of fixed locations in a visual field are determined. Such tests involve a number of selectible patterns, such as central 24, 30 or 60 patterns, peripheral 30/60 patterns, nasal step, temporal crescent and neurological patterns, as well as a central-10, 76 point pattern shown in FIG. 1.

Such static perimeter testing has been automated in the Octopus 201 analyzer sold by Interzeag AG and in the Humphrey Field Analyzer sold by Allegran Humphrey of San Leandro, Calif. Both instruments have pre-settable threshold values for a given visual field which define a normal visual field for a particular individual, taking into account the individual's age, among other factors.

The perimeter data is printed in the form of the visual field pattern, with each point in the visual field being indicated by a specific light sensitivity value, FIG. 2A, a qualitative, symbolic representation indicating a normalcy or defect condition at each stimuli point or a quantitative display using a grey scale representation of the value of each point with respect to a threshold normal value, FIG. 2B. Such measurements provide the practitioner with an indication of the presence of any localized defect or any overall defect in the visual field.

Comparing a series of successive perimeter tests taken over a period of time, FIG. 2C, for the same patient enables the practitioner to determine the progress of a disease. The ability to diagnose the onset of a particular disease or to determine the effects of treatment on a particular eye disease are extremely valuable to the practitioner.

However, the practitioner must compare each test output with preceding and succeeding tests to determine any emerging patterns over the course of numerous tests. Even if the plurality of perimeter test results are printed in a successive arrangement, it is still difficult for the practitioner to easily and quickly detect any emerging patterns without time consuming, careful analysis.

Thus, it would be desirable to provide a method for analyzing visual fields which simplifies the review of such data insofar as enabling the practitioner to easily and quickly determine emerging patterns of disease progress or retraction. It would also be desirable to provide serial visual field test data collected over a number of successive tests on a given patient in a form which is easily understandable.

SUMMARY OF THE INVENTION

The present invention is a method of analyzing serial visual fields to aid in the diagnosis of eye disorders.

In one embodiment, the present method utilizes multi-dimensional vector analysis including the steps of successively generating a plurality of time spaced, multi-point visual fields representative of eye point sensitivity of a given patient, calculating a total field vector representative of the overall state of each visual field; calculating an age normal field vector representative of an overall state of an age normal visual field for a given patient, calculating a multi-dimensional visual field analysis loss according to the equation:

$$MDVFA\ LOSS = 100 \cdot (|NFV| - |TFV|) \div |NFV|$$

where MDVFA LOSS is the multi-dimensional vector field analysis loss index, NFV is the normal field vector and TFV is the total field vector and graphically plotting the MDVFA LOSS for each visual field over the total number of visual field tests to illustrate the progression of visual field changes.

The present method also includes the further steps of calculating the vector angle between the total field vector and the normal field vector, calculating an MDVFA angle according to the equation:

$$MDVFA\ ANGLE = 100 \cdot VA \div (\pi \div 2)$$

where MDVFA ANGLE is the multi-dimensional vector field analysis angle index and VA is the vector angle and graphically plotting the MDVFA ANGLE for each visual field over the total number of visual field tests to illustrate the progression of visual field changes.

Further, the MDVFA ANGLE can be graphically plotted versus the MDVFA LOSS for a plurality of time-spaced, successive tests on a given patient to illustrate the nature of visual field changes.

In another embodiment, the present method displays serial visual fields representative of multi-point eye sensitivity including the steps of:

a. Accumulating a plurality of time-spaced multi-point visual fields representative of eye point sensitivity for a given patient, each visual field including data specifying the sensitivity for each eye point;

b. Establishing a predetermined patient base line visual field for each eye point in the visual field for a given patient;

c. Calculating the difference, point by point, for each point in each time spaced visual field test and the corresponding point in the base line visual field;

d. Graphically plotting the difference for each point as a line symmetrical about a zero axis, with the length of the line being proportional to the total number of visual field tests for a given patient; and e. Repeating steps c and d for each tested visual field to generate a serial display for each point in the tested visual field depicting the progression of visual field changes over the total number of tested visual fields.

A time regression function and a chi-squared value is calculated to determine the fit of the curve and the trend of any visual field changes. These values are graphically plotted by a computer executing a stored program, with the results displayed on either a visual display and/or a printed copy.

In a preferred embodiment, a computer is utilized and executes a stored program. The computer receives ASCII output data from peripheral tests, such as output data from an Octopus 201 Analyzer or a Humphrey Field Analyzer. The computer converts such data and stores the converted data with prior given patient data in a record file. The computer, executing the stored control program, manipulates the data to calculate the total and normal visual field vectors, the vector angle, MDVFA ANGLE and MDVFA LOSS, as well as graphically plotting the magnitude of eye sensitivity with respect to a threshold value for each eye point in the visual field. This information is graphically displayed on a computer display or on a printed copy.

The method of analyzing visual fields according to the present invention overcomes problems encountered with previous attempts to analyze such visual field data. The present method displays the results of a series of visual field tests on a given patient in an easily readable and interpretable form. As such, the eye care practitioner can quickly and easily determine the onset or progress of eye disease as well as the effectiveness of treatment. The present method is also usable with any type of automated visual field test equipment which outputs ASCII data.

The present method enables the practitioner to rapidly evaluate the indices of diffuse and local visual field change as well as point-by-point changes in serial visual fields. The use of time regression analysis additionally reveals significant trends in changes and threshold sensitivity. Finally, the output generated by the present method is presented in standardized form regardless of the particular parameter or visual field test pattern employed.

BRIEF DESCRIPTION OF THE DRAWINGS

The various features, advantages and other uses of the present invention will become more apparent by referring to the following detailed description and drawing in which.

DESCRIPTION OF THE PREFERRED EMBODIMENTS

Figure 1:
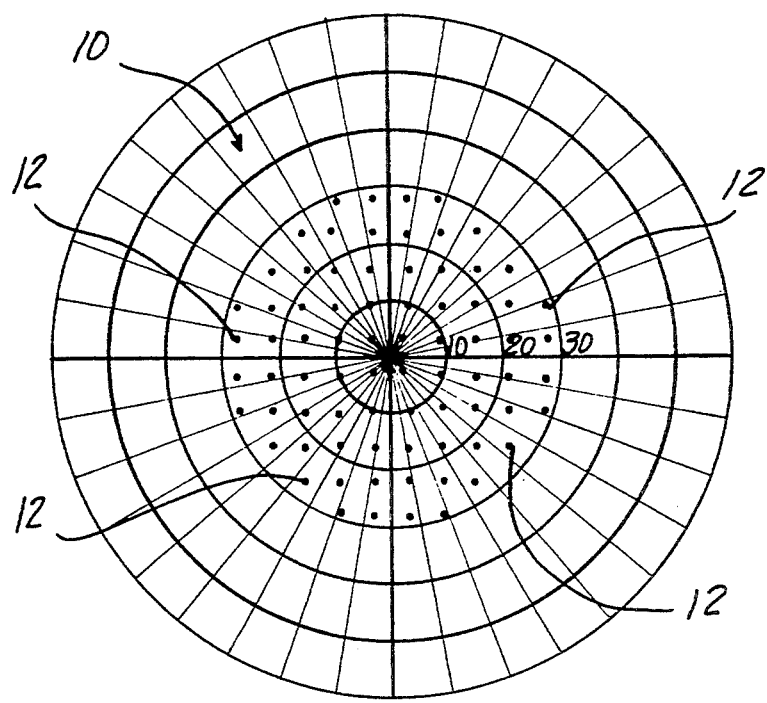
FIG. 1 is a graphic display of the eye points in a central 30 degree, 76 point visual field test pattern.
Figure 3:
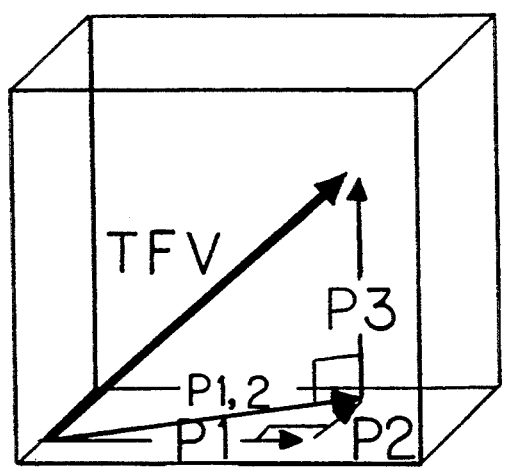
FIG. 3 is a graph showing the calculation of the total field vector according to the present invention.

By way of background, reference number 12 in FIG. 1 depicts the 76 points in a central 30 degree visual field test pattern for a human patient's right or left eye. According to the present method of analyzing serial visual fields, 74 points, excluding the point in the blind spot, are employed to calculate a 74 dimensional total field vector (TFV). For clarity in understanding the concept of the present method, a simple visual field consisting of only three points whose sensitivities are $P_1$, $P_2$ and $P_3$ are shown in FIG. 3. A three-dimensional vector space is formed by assigning a vector P to each point. The length of each vector is proportional to the sensitivity of the point and the direction of the vector is perpendicular (orthogonal) to all other vectors. The vectors are added together using conventional vector addition to obtain the total field vector (TFV) as shown in FIG. 3. The assumption of independence of each point in the visual field to allow for the assignment of each point to an orthogonal dimension is substantially correct. Although there is some correlation between the value of each point measured in the visual field and the values of its neighbors, as long as the vector assignments are consistently made, the results will be useful and consistently related to each other as described thereafter.

The length of the TFV is determined by using the Pythagorean Theorem as follows:

$$|TFV| = (P_1^2 + P_2^2 + P_3^2 + \ldots P_n^2)^{\frac{1}{2}} \quad (1)$$

where n is the total number of visual field points (74 in the present example)

Figure 4:
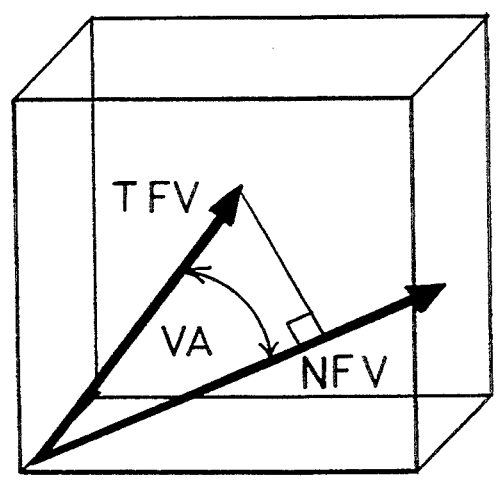
FIG. 4 is a graph depicting the calculation of the vector angle between the total field vector and the normal field vector according to the present invention.
Figure 2A:
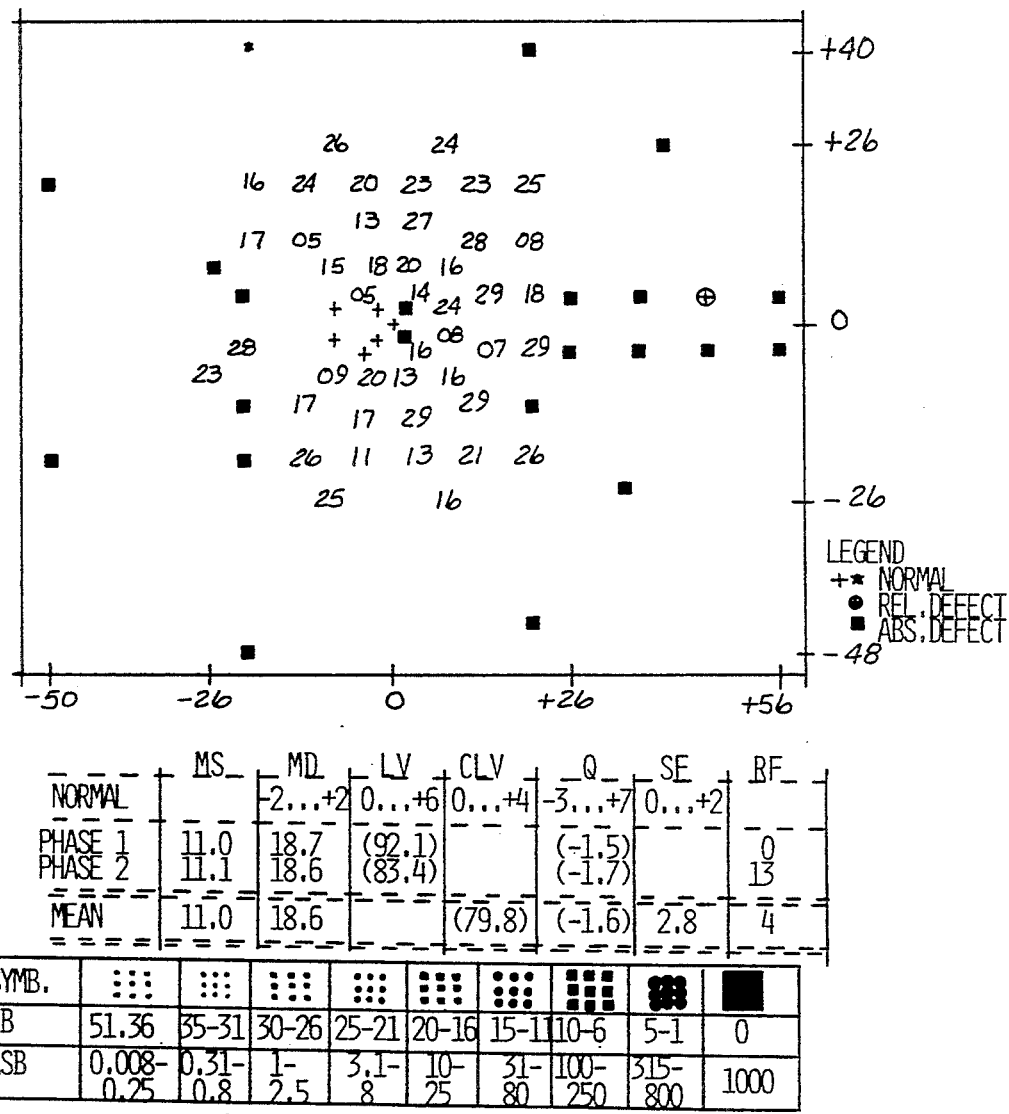
FIG. 2A is a representation of the output of an Octopus analyzer showing the sensitivity values for the central and some peripheral points in the visual field.
Figure 2B:
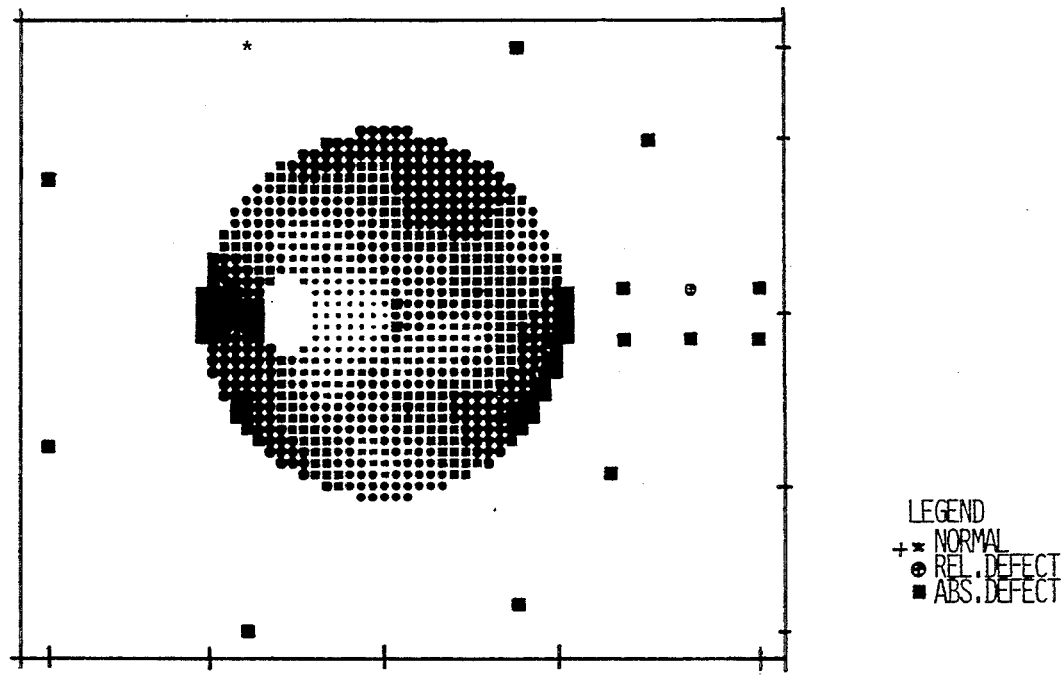
FIG. 2B is a gray scale representation of the sensitivity values shown in FIG. 2A.
Figure 2C:
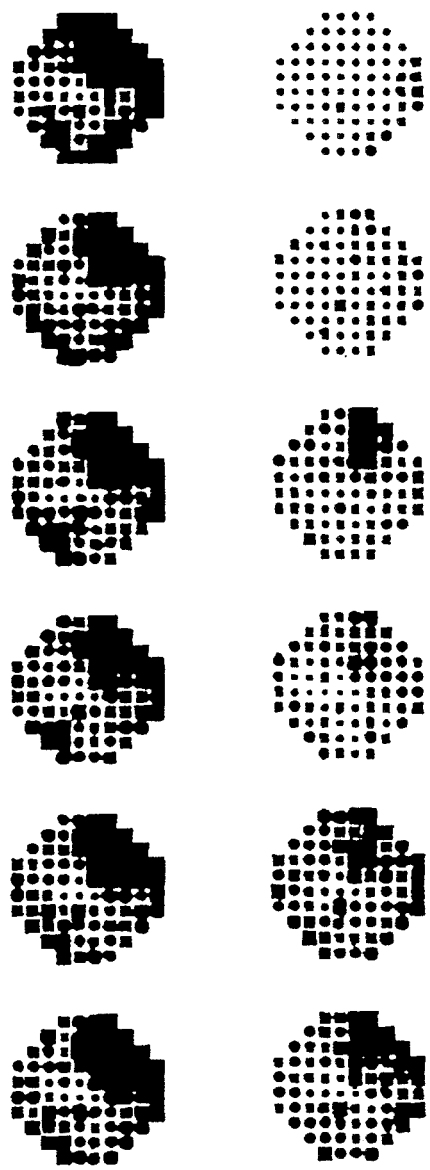
FIG. 2C is a graphic representation of a series of gray scale outputs for a given patient over a given period of time.

The TFV has a length and a direction. The direction of the TFV is referenced to an age normal visual field vector (NFV). The NFV is generated according to equation (1) above for a normal visual field representative of a given patient age or, alternately, a predetermined patient baseline visual field. The vector angle (VA) between the TFV and the NFV can be calculated from the vector dot product between the TFV and NFV as shown in FIG. 4. The vector dot product is defined as the product of the length of the NFV with the length of the perpendicular projection of the TFV onto the NFV. The vector dot product is defined as:

$$TFV \cdot NFV = \Sigma T_i \cdot N_i = |TFV| \cdot |NFV| \cdot \cos(VA) \quad (2)$$

where $\Sigma T_i \cdot N_i = T_1 \cdot N_1 + T_2 \cdot N_2 + \ldots T_n \cdot N_n$ n=74 in the present example and $T_i$ and $N_i$ are the $i^{th}$ components of the TFV and the NFV, respectively.

The angle between TFV and NFV can be found by solving equation (2) for VA as follows:

$$VA = \arccos((\Sigma T_i \cdot N_i) \div (|TFV| \cdot |NFV|)) \quad (3)$$

The length of the vectors TFV and NFV are represented by |TFV| and |NFV| to distinguish them from the actual vector quantities.

The multi-dimensional vector field analysis method of present invention requires linearization of the sensitivity values of the field to calculate the vector angle VA while the actual sensitivities in dB (log units) are used to calculate the |TFV| and |NFV| otherwise. This necessity results from the difference in mapping length and angle quantities in the vector space when the field values are non-linear units (dB). In order to maintain angles under uniform scaling, it is necessary to linearize the values of the sensitivities of points used to calculate VA, i.e., $T_i$, $N_i$, |TFV| and |NFV|, in equation (3) by the following conversion:

$$\text{Linear Value of } P_i = 10^{P_i/10} \quad (4)$$

where $P_i$=sensitivity (in dB) of the point i

According to the present method, the calculated values of |NFV|, |TFV| and VA for each tested visual field are used to calculate a set of global indices, i.e., the MDVFA LOSS and the MDVFA ANGLE. The MDVFA LOSS and the MDVFA ANGLE calculations were carried out for a plurality of serial visual fields for each patient, with five serial exams being shown in FIGS. 5 and 6. The |TFV|, |NFV| and VA were calculated for each visual field along with the global indices for the whole field, the upper and lower hemifields, and the temporal, nasal, upper and lower quadrants. The multi-dimensional vector field analysis values are calculated as follows:

$$MDVFA \text{ LOSS} = 100 \cdot (|NFV| - |TFV|) \div |NFV| \quad (5)$$

$$MDVFA \text{ ANGLE} = 100 \cdot VA \div (\pi/2) \quad (6)$$

Figure 5A:
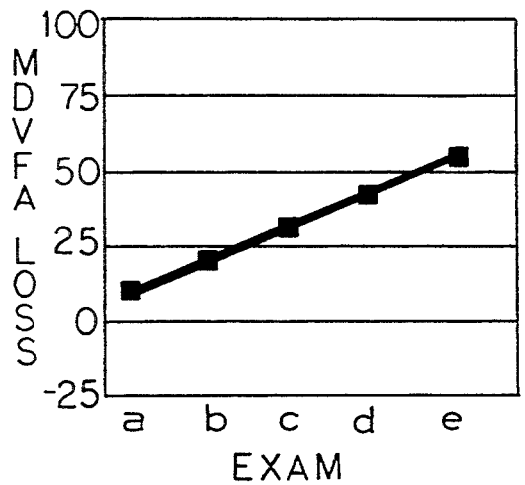
FIGS. 5A and 6A are graphs showing the MDVFA LOSS over a series of exams.
Figure 5B:
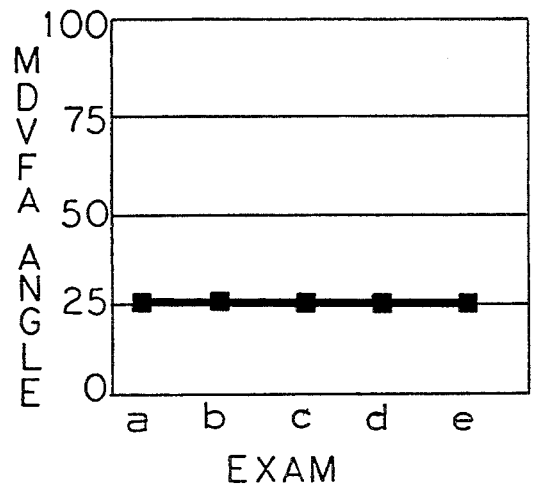
FIGS. 5B and 6B are graphs showing the MDVFA ANGLE over a series of exams.

The effect of a uniform reduction of sensitivity in the visual field due to a cataract or diffuse glaucomatous loss leads to a reduction in |TFV|, but does not result in a significant change in the VA. This is illustrated in FIGS. 5A and 5B for five exams on a given patient. It should be noted that the data in FIGS. 5A and 5B and the following graphs are presented for serial conducted exams and are not displayed as a function of time. As shown in FIG. 5A, the visual field starts out with a 3 dB uniform depression of sensitivity and then uniformly decreases 3 dB with each subsequent exam. The MDVFA LOSS increases uniformly with each exam, but the MDVFA ANGLE remains unchanged as shown in FIG. 5B.

Figure 6A:
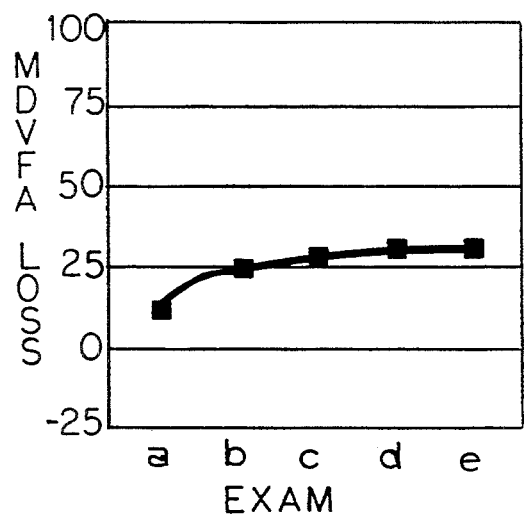
Figure 6B:
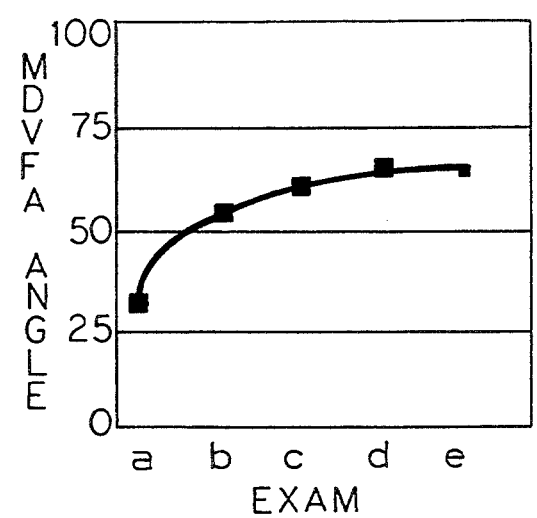
Figure 7A:
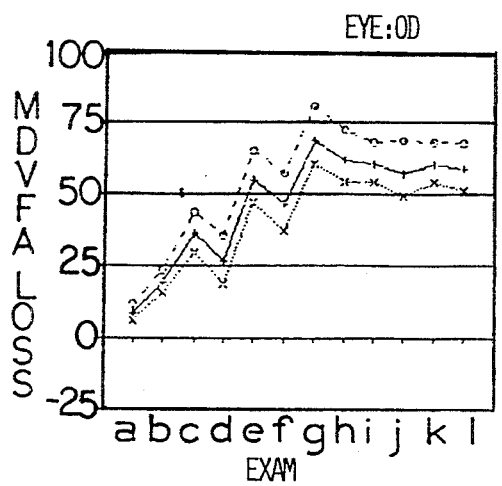
FIGS. 7A-7D are graphs depicting MDVFA LOSS, MDVFA ANGLE, % MEAN DEFECT and $LOG_{10}$ CLV, respectively, over a series of exams.
Figure 7B:
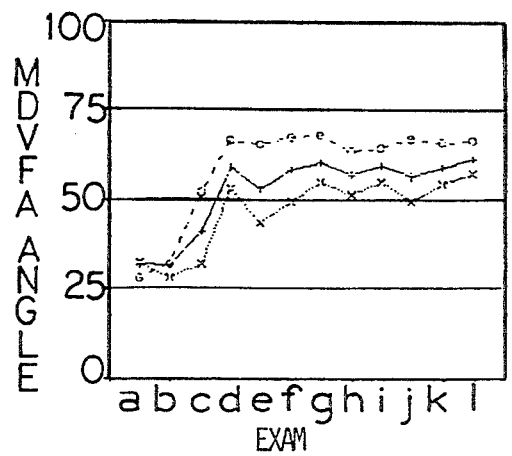
Figure 7C:
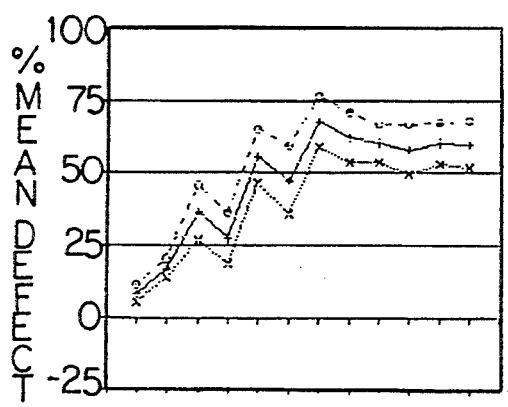
Figure 7D:
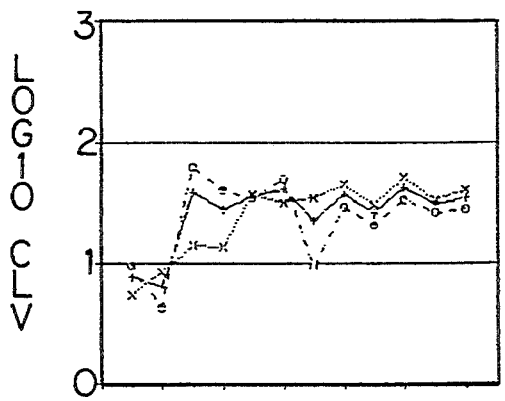

In the case of a localized defect in the visual field, there will be a non-uniform reduction of the sensitivities of the points in the visual field. An example of such a localized defect might be a glaucomatous scotoma. The effect of a non-uniform reduction of the field values leads to a reduction of both of the length of the TFV with respect to the NFV and a change in the VA with respect to the NFV. This is illustrated in FIGS. 6A and 6B. In this example, an initial, limited scotoma deepens without spreading in each successive exam as shown in FIG. 6A. Thus, the MDVFA LOSS increases until reaching a limit; while the MDVFA ANGLE rises rapidly initially and also saturates at a limit as the scotoma becomes absolute as shown in FIG. 6B.

FIGS. 7A–7D depict similar MDVFA LOSS and MDVFA ANGLE calculations over a series of twelve exams for a given patient. For purposes of comparison, the global indices of MDVFA LOSS and MDVFA ANGLE are compared to standard global indices of Mean Defect and Correct Loss Variance (CLV) values for the twelve exams. These standard global indices are calculated as follows:

$$\% \text{ MEAN DEFECT} = 100 \cdot \text{Mean Defect} \div \text{Age Normal Mean Sensitivity} \quad (7)$$

$$\text{LOG 10 CLV} - \log_{10} \text{CLV} \quad (8)$$

Thus, the MDVFA LOSS and MDVFA ANGLE global indices according to the present invention correlate with the % MEAN DEFECT and corrected loss variance (CLV) indices of previously devised visual field analysis techniques.

Figure 8:
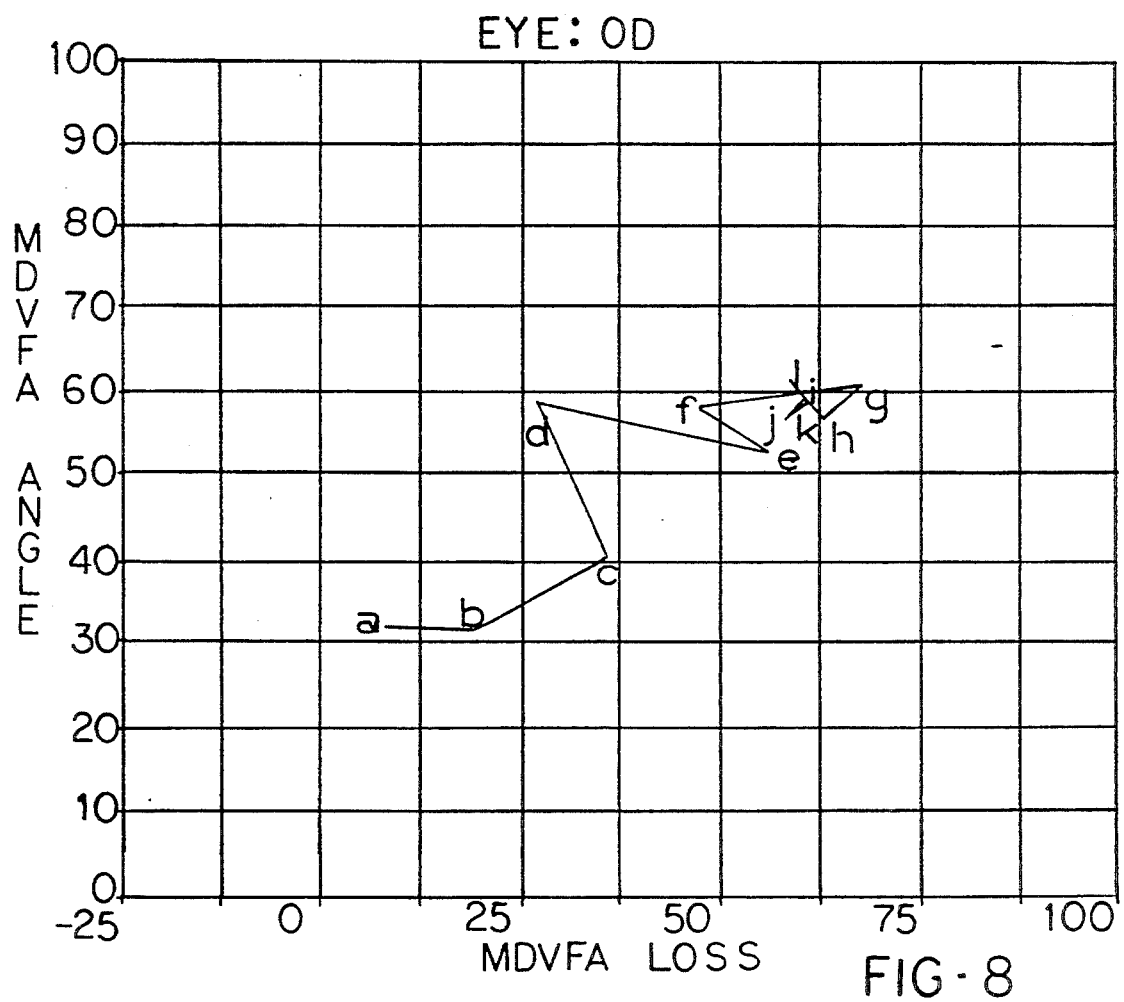
FIG. 8 is a graph plotting MDVFA ANGLE against MDVFA LOSS over a series of exams.
Figure 9:
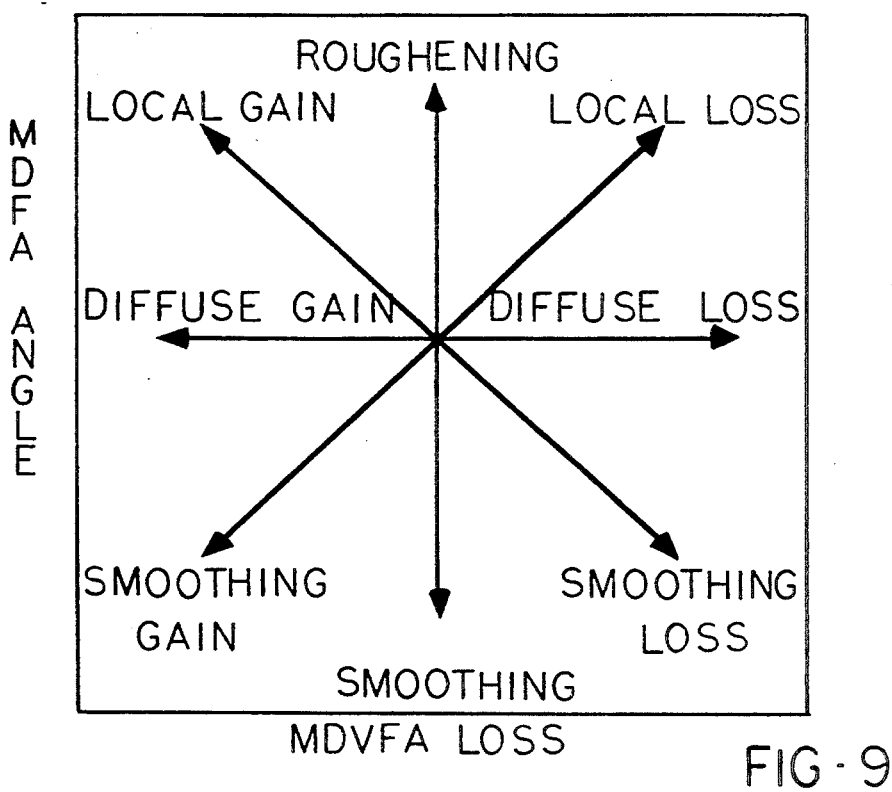
FIG. 9 is a graphic representation of the interpolation of trends in visual field changes for the graph shown in FIG. 8.

The TFV traces out a path in n-dimensional space as the visual field which it represents changes with time. The two quantities |TFV| and VA describe the general state of the visual field. The MDVFA LOSS and MDVFA ANGLE correspond to changes in the |TFV| and VA, respectively. The MDVFA ANGLE may be graphically plotted against MDVFA LOSS for a series of exams to generate the path or "trajectory" corresponding to the changes in the visual field so as to understand the nature of the changes in the visual field without recourse to the entire visual field data. FIG. 8 depicts a diagram of MDVFA ANGLE versus MDVFA LOSS and indicates the changes in the visual field when these values are plotted in two dimensions. FIG. 9 depicts a generalization of the trends or direction of the trajectory of the segments shown in the graph in FIG. 8. For example, a change in the direction of the trajectory toward the upper half of the diagram in FIG. 9 indicates increasing non-uniformity in the distribution of field sensitivities. A change in the direction of the trajectory toward the lower half indicates a smoothing or levelling of the distribution of sensitivities. A change in the direction of the trajectory toward the right of the diagram in FIG. 9 corresponds to increasing diffuse loss; while a change to the left indicates a diffuse improvement in sensitivity.

In a preferred embodiment, the various calculations described above and the graphic plotting of the MDVFA LOSS, MDVFA ANGLE and MDVFA ANGLE versus MDVFA LOSS are performed by a computer executing a stored control program. The details of the computer program in performing this embodiment of the present method will be described in greater detail hereafter.

Figure 10:
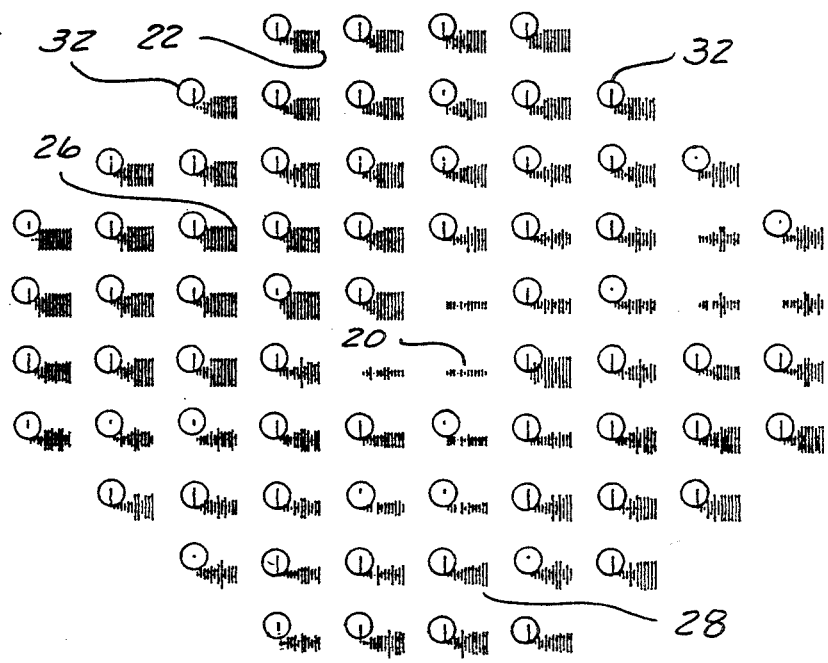
FIG. 10 is a serial graphic display of the sensitivity differences for each point in a visual field over a number of exams of the Octopus program 32 for a given patient.
Figure 11:
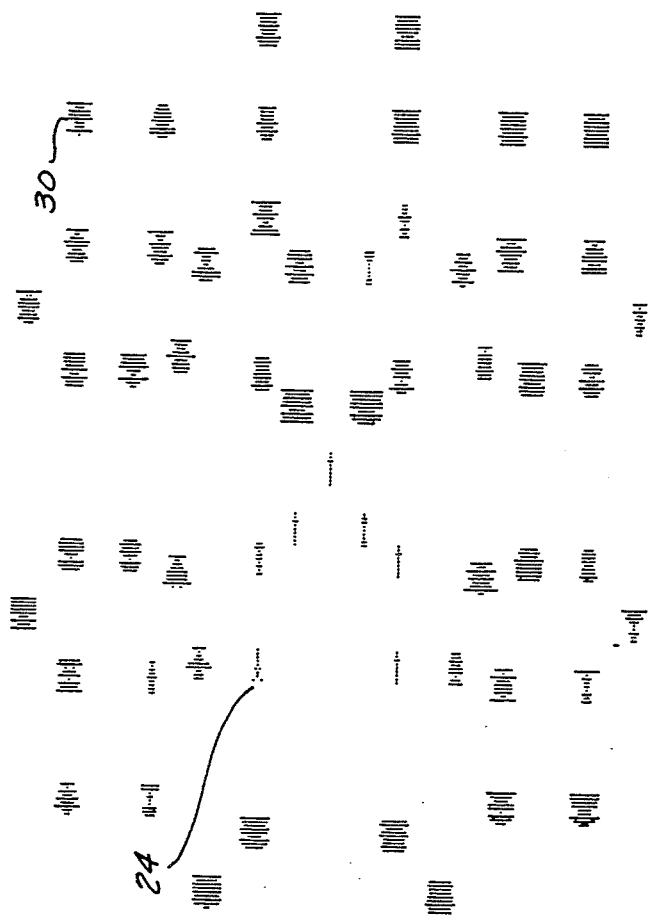
FIG. 11 is a serial graphic display of the sensitivity differences of the Octopus program 32 for a different patient.

According to another embodiment of the present invention, a serial graphic display of each point in the visual field is generated for a plurality of visual fields, such as 16, each representing a different time-spaced visual field test on a given patient. A plurality of visual fields, such as a maximum of 16, and a total of 1216 points may be displayed on a single graph as shown in FIGS. 10 and 11. In this embodiment of the present method, actual numeric data from a visual field test, such as that output in ASCII code from an Octopus 201 Analyzer or a Humphrey Field Analyzer, for example, is first accumulated for each visual field test. This data is compared, point by point, in each visual field with a predetermined reference value or base line. The reference value may be an age-adjusted normal value or the value of a given patient's baseline test. The actual visual field data for each visual field point and the corresponding reference value are compared and a difference value denoted by ΔS reflecting the relative change in sensitivity for each point is generated.

The ΔS is displayed as a vertical line of a predetermined, variable length symmetrically placed about a zero axis for each point in the visual field. The ratio: R=ΔS÷display line length, is used as a vertical scaling factor. By example only, R is set at 4 dB per symmetric pixel pair to show the full range of possible change. A single dot shown by reference number 20 in FIG. 10 depicts the zero axis and reflects no significant change in the visual field at the specified point in one exam. The vertical lines of varying length, such as lines 22 in FIG. 10, reflect varying ΔS at the same point in prior or subsequent visual field tests. In FIGS. 10 and 11, a solid line represents a loss in sensitivity (ΔS≦0); while a vertical space bounded by dots indicates a gain in sensitivity (ΔS≧0) as shown by reference number 24 in FIG. 11.

In interpreting the results of the serial graphic displays shown in FIGS. 10 and 11, which are each serial graphic displays for a different patient, reference numeral 26 depicts the change in eye sensitivity for a given point in the first patient. These constant length vertical lines indicates an absolute, stable loss in eye sensitivity at the specified visual field point. The test results at the eye point shown by reference numeral 28 in FIG. 10 in which the length of the vertical lines increase over successive tests shows a significant linear loss trend. Reference numeral 30 in FIG. 11 shows a deterioration in eye sensitivity followed by a brief improvement and then subsequent deterioration.

A linear regression is then performed for ΔS versus time at each point measured in each visual field. A chi-square test is used to find the "goodness of fit" of the regression line. Significance bars denoted by reference number 32 in FIG. 10 depict the significance of the fit, with the length of the bar indicating the degree of significance of the fit. An upwardly extending bar above the zero axis depicts a deteriorating eye sensitivity, while a downwardly extending bar indicates an improving sensitivity.

Figure 12A:
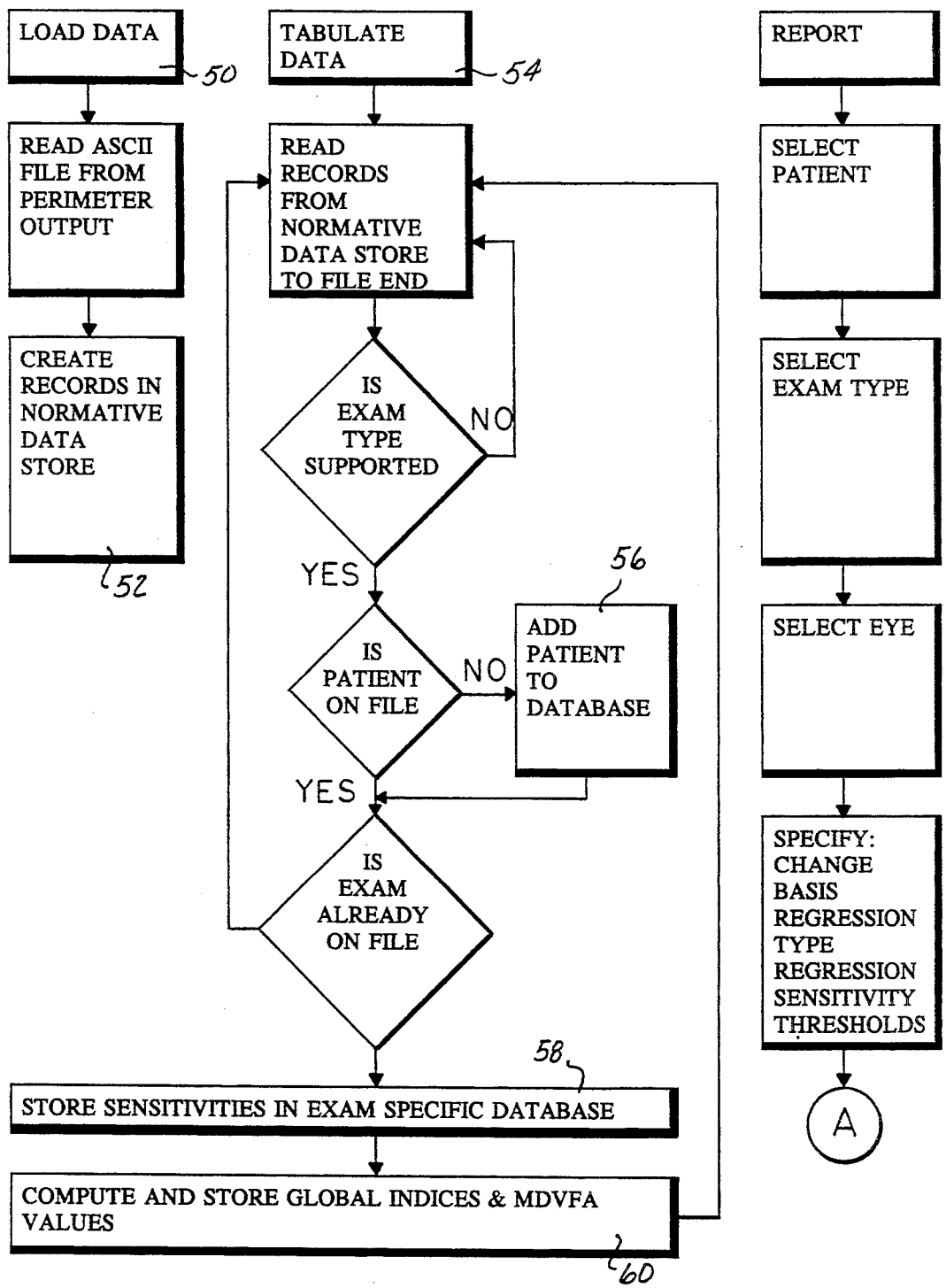
FIGS. 12A-12C are flow diagrams of the control program executed by a computer in performing the method of the present invention.

As noted above, in a preferred embodiment, a computer executing a stored control program is employed to perform the various calculations on field analyzer data to generate the various global indices, graphic plots and serial graphic displays for a series of visual field tests on a given patient. The software program is depicted generally in FIGS. 12A–12C. In step 50, FIG. 12A, data from a field analyzer in ASCII form is input into the computer and stored in a normative data store in step 52. This data is then tabulated in step 54 and, either a new file is opened for a new patient in step 56 or the data is added to an existing patient file in step 58. The global indices, namely, MDVFA LOSS and MDVFA ANGLE are then calculated in step 60 for all of the visual field test data for a given patient.

Figure 12B:
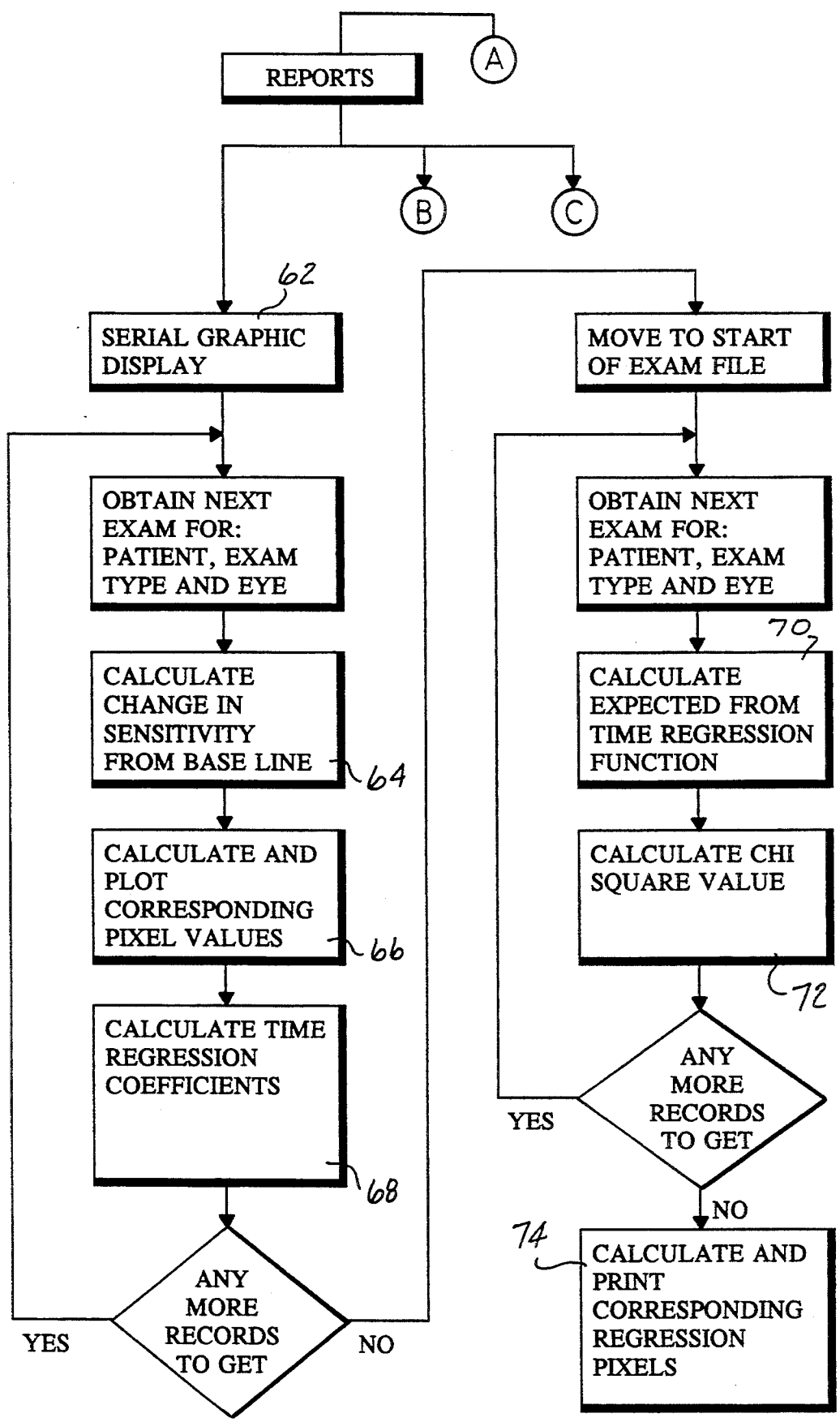

In FIG. 12B, various reports can be selected to generate the desired output needed by an eye care practitioner to diagnose and treat eye disorders. When the serial graphic display report is selected in step 62, the computer program calculates the changes in sensitivity from the base line or reference value in step 64 for each visual field test on a given patient. The control program calculates and plots the corresponding pixel values for display in the serial graphic display in step 66. The time regression coefficients are next calculated in step 68 for each visual field test. The time regression function is then calculated in step 70 for all of the stored visual field tests on a given patient and the "goodness of fit" is calculated in step 72 by performing a chi-squared test. These pixel values and significance indicators are then graphically plotted in step 74, either on a computer display or on a printed copy or both.

Figure 12C:
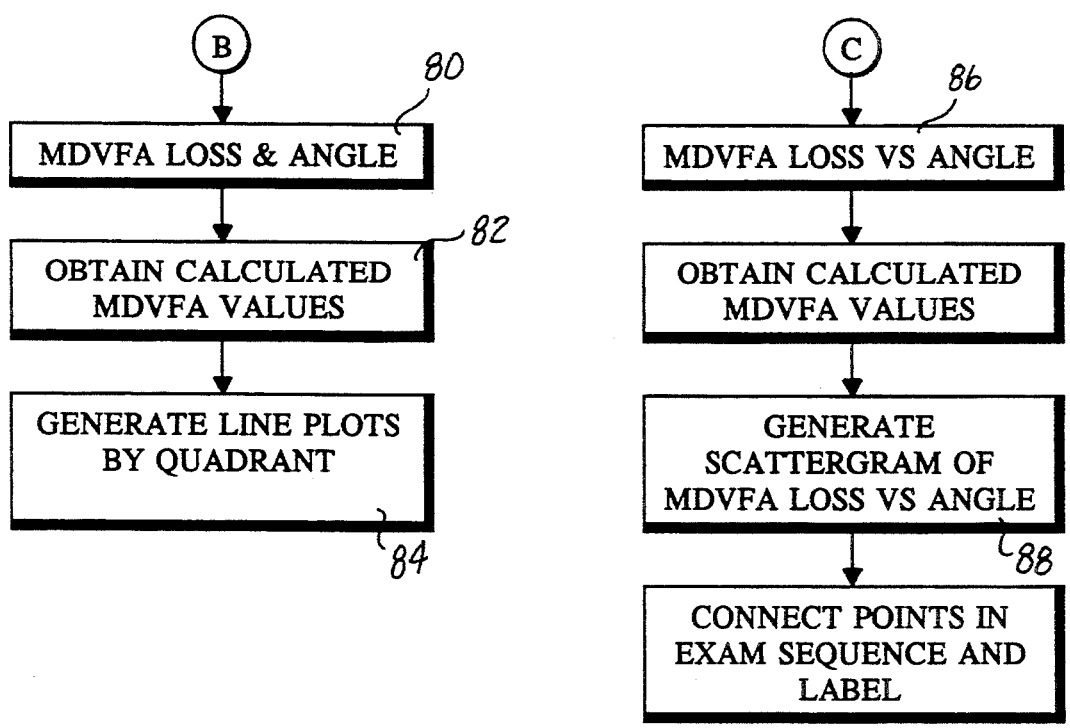

When the multi-dimensional vector field analysis report is desired, as shown in FIG. 12C, the control program first calculates the MDVFA LOSS and the MDVFA ANGLE for each visual field test on a given patient. This is indicated in step 80 in FIG. 12C. The MDVFA values are then calculated in step 82 and graphically plotted by quadrant in step 84. The MDVFA ANGLE versus MDVFA LOSS plot is then generated in step 86. The control program calculates the appropriate MDVFA values and graphically plots the MDVFA ANGLE versus MDVFA LOSS and connects the various points as described above and shown in FIG. 8.

In summary, there has been disclosed a unique method for analyzing serial visual fields in which global indices are calculated and graphically plotted to indicate trends or changes in eye sensitivity over a series of visual field tests. Further, a serial graphic display can be generated to plot the change in sensitivity for each point in a visual field over a plurality of visual field tests which combines in a single display all of the changes in eye sensitivity at each point in the tested visual field over the series of tests. Both techniques enable an eye care practitioner to determine changes or trends in visual field loss or improvement. The visual field data is reduced to two-dimensional plots which characterize the state of the visual field. The serial graphic display makes it possible, in a series of visual fields, to identify subtle patterns of local changes not apparent from generalized field indices alone.

Further, the method of the present invention is not specific to a single test program or to an Octopus or Humphrey perimeter test. Thus, the method of the present invention presents a uniform graphic output for the results of serial visual field examinations on a wide range of different instruments.

What is claimed is:

1. A method of analyzing serial visual field data representative of multi-point eye sensitivity to detect visual field changes, the method comprising the steps of:

successively generating a plurality of time spaced, multi-point visual fields from a visual field analyzer, the visual fields representative of eye point sensitivity for a given patient, each visual field including data indicative of the sensitivity of each of a plurality of eye points in each visual field;

calculating a total field vector (TFV) representative of the overall state of each visual field;

calculating an age normal field vector (NFV) representative of the overall state of an age normal visual field for a given patient;

calculating a multi-dimensional visual field analysis loss (MDVFA LOSS) according to the equation:

$$MDVFA\ LOSS = 100 \cdot (|NFV| - |TFV|) \div |NFV|;$$

graphically plotting the MDVFA LOSS for each visual field over the total number of visual fields to display the progression of visual field changes in a single plot;

calculating the vector angle (VA) between the TFV and the NFV;

calculating an MDVFA ANGLE according to the equation:

$$MDVFA\ ANGLE = 100 \cdot VA \div (\pi/2);$$

graphically plotting the MDVFA ANGLE for each visual field over the total number of visual fields to display the progression of visual field changes in a single plot; and comparing the plotted MDVFA loss and the plotted MDVFA ANGLE over the total number of visual fields to determine the progression of visual field changes.

2. The method of claim 1 wherein the vector angle (VA) is calculated by:

$$VA = \text{arcCos}\left((\Sigma T_i N_i) \div (|TFV| \cdot |NFV|)\right)$$

where $T_n$ and $N_n$ are the $n^{th}$ components of the TFV and the NFV, respectively.

3. The method of claim 1 further including the step of:

graphically plotting MDVFA ANGLE versus MDVFA LOSS for a plurality of time-spaced, successive visual field tests on a given patient, the direction of the plotted MDVFA ANGLE versus MDVFA LOSS from a first visual field to a last visual field indicative of variations in the uniformity of visual field changes and variations in the local and diffuse visual field changes.

4. A method of displaying serial visual fields representative of multi-point eye sensitivity comprising the steps of:

a. accumulating a plurality of time-spaced multi-point visual fields from a visual filed analyzer for a given patient representative of eye point sensitivity, each visual field including data indicative of the sensitivity for each eye point;

b. establishing a predetermined patient base line visual field for each eye point in the visual field for a given patient;

c. calculating the difference, eye point by eye point, for each eye point in each time spaced visual field and the corresponding eye point in the base line visual field;

d. graphically plotting the difference for each eye point as an indicia having first and second end points spaced symmetrically about a zero axis, with the distance between the first and second end points being proportional to the calculated difference between the sensitivity of each eye point and the sensitivity of the base line of each eye point of a given patient;

e. repeating steps c and d for each tested visual field;

f. serially arranging the plurality of indicia for each eye point from all of the time spaced visual fields on an eye point by eye point basis in consecutive visual field test order to depict the progression of visual field changes for each eye point over the total number of tested visual fields.

5. The method of claim 4 further including the step of:

performing a time regression function on the eye point sensitivity change for each eye point over all of the tested visual fields.

6. The method of claim 5 further including the steps of:

performing a chi-squared test on the time regression function; and plotting a bar adjacent each serial arrangement of plotted eye point indicia whose length is proportional to the degree of significance of the fit of the linear regression function and whose direction from the zero axis is indicative of the direction of change of the eye point sensitivity.

7. The method of claim 4 wherein the step of graphically plotting is performed by a computer which displays the results in at least one of a visual display and a printed copy.

8. The method of claim 4 further comprising the steps of:

depicting the indicia representing a loss in eye point sensitivity for each eye point from the patient base line as a line extending between the first and second end points; and depicting the indicia representing a gain in eye point sensitivity for each eye point from the patient base line as a dot at each of the first and second end points.

* * * * *